(12) United States Patent
Ma et al.

(10) Patent No.: US 7,323,562 B2
(45) Date of Patent: Jan. 29, 2008

(54) METHOD OF PREPARING POLY(ADP-RIBOSE) POLYMERASES INHIBITORS

(75) Inventors: Chunrong Ma, San Diego, CA (US); Naresh Nayyar, San Diego, CA (US); Nebojsa Slobodan Stanković, La Jolla, CA (US)

(73) Assignees: Agouron Pharmaceuticals, Inc., San Diego, CA (US); Cancer Research Technology Ltd., London (GB)

( * ) Notice: Subject to any disclaimer, the term of this patent is extended or adjusted under 35 U.S.C. 154(b) by 0 days.

(21) Appl. No.: 11/233,845

(22) Filed: Sep. 21, 2005

(65) Prior Publication Data

US 2006/0063926 A1    Mar. 23, 2006

Related U.S. Application Data

(60) Provisional application No. 60/612,457, filed on Sep. 22, 2004.

(51) Int. Cl.
C07D 487/06    (2006.01)

(52) U.S. Cl. ...................................................... 540/520
(58) Field of Classification Search ................. 540/520
See application file for complete search history.

(56) References Cited

U.S. PATENT DOCUMENTS 6,495,541 B1    12/2002    Webber et al.

FOREIGN PATENT DOCUMENTS

| LB | 6934 | 6/2004 |
|---|---|---|
| WO | WO 00/42040 | 7/2000 |
| WO | PCT/IB2004/000915 | 10/2004 |

*Primary Examiner*—Bruck Kifle
(74) *Attorney, Agent, or Firm*—Bryan C. Zielinski; Galina M. Yakovleva

(57) ABSTRACT

This invention relates to a new and convergent route to small molecule inhibitors of poly(ADP-ribose) polymerase, such as 8-fluoro-2-{4-[(methylamino)methyl]phenyl}-1,3,4,5-tetrahydro-6H-azepino[5,4,3-cd]indol-6-one, via a key Sonogashira coupling reaction and a CuI-promoted indole formation.

8 Claims, No Drawings

METHOD OF PREPARING POLY(ADP-RIBOSE) POLYMERASES INHIBITORS

This application claims the benefit of U.S. Provisional Application No. 60/612,457 filed on Sep. 22, 2204, the contents of which is hereby incorporated by reference in its entirety.

FIELD OF THE INVENTION

This invention generally relates to methods of preparing compounds that inhibit poly(ADP-ribose) polymerases, thereby retarding the repair of damage to DNA strands. The inventive method is particularly useful in preparing compounds that are useful for potentiation of anti-cancer therapies.

BACKGROUND OF THE INVENTION

The compound 8-fluoro-2-{4-[(methylamino)methyl]phenyl}-1,3,4,5-tetrahydro-6H-azepino[5,4,3-cd]indol-6-one represented by formula

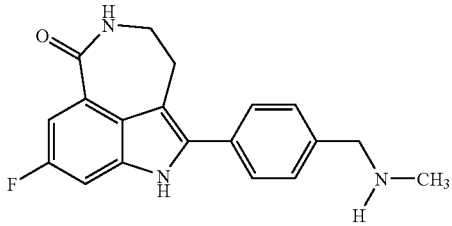

is a small molecule inhibitor of poly(ADP-ribose) polymerase (PARP). 8-Fluoro-2-{4-[(methylamino)methyl]phenyl}-1,3,4,5-tetrahydro-6H-azepino[5,4,3-cd]indol-6-one and salts thereof, is disclosed in U.S. Pat. No. 6,495,541 and PCT. Application. No. PCT/IB2004/000915, International Publication No. WO 2004/087713, the disclosures of which are incorporated herein by reference in their entireties. U.S. Provisional Patent Application Nos. 60/612,459 and 60/679,296, entitled "Polymorphic Forms of the Phosphate Salt of 8-Fluoro-2-{4-[(methylamino)methyl]phenyl}-1,3,4,5-tetrahydro-6H-azepino[5,4,3-cd]indol-6-one," the disclosures of which are incorporated herein by reference in their entireties, describe novel polymorphic forms of the phosphate salt of 8-fluoro-2-{4-[(methylamino)methyl]phenyl}-1,3,4,5-tetrahydro-6H-azepino[5,4,3-cd]indol-6-one, and methods for their preparation. U.S. Provisional Patent Application Nos. 60/612,458; and 60/683,006, entitled "Therapeutic Combinations Comprising Poly(ADP-Ribose) Polymerases Inhibitor," the disclosures of which are incorporated herein by reference in its entirety, describe pharmaceutical combinations of 8-fluoro-2-{4-[(methylamino)methyl]phenyl}-1,3,4,5-tetrahydro-6H-azepino[5,4,3-cd]indol-6-one.

To date, eighteen enzymes have been identified by DNA sequence homology in the PARP family and the biochemical and enzymatic properties of seven have been investigated: PARP-1, and PARP-2 are stimulated by DNA strand breaks, PARP-3 interacts with PARP-1 and the centrosome, PARP-4 also known as vault PARP (VPARP) is the largest PARP and is associated with cytoplasmic vaults, tankyrase 1 and 2 (PARP-5a and 5b) are associated with telomeric proteins and the function of PARP-7 (TiPARP) is not clear at present but it may be involved in T-cell function and it can poly(ADP-ribosylate) histones (Ame J C, Splenlehauer C and de Murcia G. The PARP Superfamily. *Bioessays* 26 882-893 (2004)). Pharmacology studies have shown that the compound of formula 1 is an inhibitor of PARP-1 ($K_i$=1.4 nM) and PARP-2 ($K_i$=0.17 nM). Based on structural similarities in the amino acid sequences among the PARP enzymes, the compound of formula 1 likely binds with high affinity to the other members of the family as well.

Enzyme-mediated repair of single- or double-strand breaks in DNA is a potential mechanism of resistance to radiotherapy or cytotoxic drugs whose mechanism depends on DNA damage. Inhibition of DNA repair enzymes is thus a strategy for the potentiation of these agents. PARP-1, the best-characterized member of the PARP family, is a nuclear enzyme that upon activation by DNA damage mediates the transfer of ADP-ribose fragments from $NAD^+$ to a number of acceptor proteins. Depending on the extent of DNA damage incurred, PARP-1 activation and subsequent poly (ADP-ribosyl)ation mediate the repair of the damaged DNA or induce cell death. When DNA damage is moderate, PARP-1 plays a significant role in the DNA repair process. Conversely, in the event of massive DNA damage, excessive activation of PARP-1 depletes ATP pools (in an effort to replenish $NAD^+$), which ultimately leads to cell mortality by necrosis (Tentori L, Portarena I, Graziani G. Potential applications of poly(ADP-ribose) polymerase (PARP) inhibitors. Pharmacol Res 2002; 45:73-85).

As the result of the dual role of PARP-1, inhibitors of this enzyme, such as 8-fluoro-2-{4-[(methylamino)methyl]phenyl}-1,3,4,5-tetrahydro-6H-azepino[5,4,3-cd]indol-6-one, may have a role as chemosensitizing agents (by preventing DNA repair, for example, after anticancer therapy), or as treatments for a variety of disease and toxic states that involve oxidative or nitric oxide induced stress and subsequent PARP hyperactivation. Such conditions include neurologic and neurodegenerative disorders (eg, Parkinson's disease, Alzheimer's disease) (Love S, Barber R, Wilcock G K. Increased poly(ADP-ribosyl)ation of nuclear proteins in Alzheimer's disease. Brain 1999; 122:247-53; Mandir A S, Przedborski S, Jackson-Lewis V, et al. Poly(ADP-ribose) polymerase activation mediates 1-methyl-4-phenyl-1,2,3,6-tetrahydropyridine (MPTP)-induced parkinsonism. Proc Natl Acad Sci USA 1999; 96:5774-9), cardiovascular disorders (eg, myocardial infarction, ischemia-reperfusion injury) (Pieper A A, Walles T, Wei G, et al. Myocardial postischemic injury is reduced by poly(ADP-ribose) polymerase-1 gene disruption. J Mol Med 2000; 6:271-82; Szabó G, Bährle S, Stumpf N, et al. Poly(ADP-ribose) polymerase inhibition reduces reperfusion injury after heart transplantation. Circ Res 2002; 90:100-6; U.S. Pat. No. 6,423,705), inflammatory diseases, (Szabó C, Dawson V. Role of poly (ADP-ribose) synthetase in inflammation and, ischaemia-reperfusion. TIPS 1998; 19:287-98), diabetic vascular dysfunction (Soriano F G, Virág L, Szabó C. Diabetic endothelial dysfunction: role of reactive oxygen and nitrogen species production and poly(ADP-ribose) polymerase activation. J Mol Med 2601; 79:437-48), arthritis (Szabó C, Virág L, Cuzzocrea S, et al. Protection against peroxynitrite-induced fibroblast injury and arthritis development by inhibition of poly(ADP-ribose) synthase. Proc Natl Acad Sci USA 1998; 95:3867-72), and cisplatin-induced nephrotoxicity (Racz I, Tory K, Gallyas F, et al. BGP-15—a novel poly(ADP-ribose) polymerase inhibitor—protects against nephrotoxicity of cisplatin without compromising its anti-tumor activity. Biochem Pharmacol 2002; 63:1099-111). Furthermore, it was shown that BRCA2 deficient tumor cells are acutely sensitive to PARP-1 inhibitors (Bryant et al. "Specific killing of BRCA2 deficient tumors with inhibitors of poly(ADP-ribose)polymerase," submitted to publication). PARP inhibitors are also involved in enhancing the induction of the expression of Reg gene in β cells and HGF gene and, accordingly, promote the proliferation of pancreatic β-cells of Langerhans' islets and suppress apoptosis of the cells (U.S. Patent Application Publication 2004/0091453; PCT Publication No. WO 02/00665). In addition, PARP inhibitors are also used in cosmetic preparations, especially in after-sun lotions (PCT Publication No. WO 01/82877). There are no marketed PARP inhibitors presently.

One method of synthesizing 8-fluoro-2-{4-[(methylamino)methyl]phenyl}-1,3,4,5-tetrahydro-6H-azepino[5,4,3-cd]indol-6-one is disclosed in the above-referenced U.S. Pat. No. 6,495,541. This method is a linear 10-step synthesis, which involves a key Leimgruber-Batcho indole formation step and a Suzuki coupling reaction. Although the current route is an effective synthetic route employed in the synthesis of toxicology and clinical batches of 8-fluoro-2-{4-[(methylamino)methyl]phenyl}-1,3,4,5-tetrahydro-6H-azepino[5,4,3-cd]indol-6-one, it would be desirable to have an alternative convergent route for eventual commercial manufacturing. The present invention provides a new and convergent route to 8-fluoro-2-{4-[(methylamino)methyl]phenyl}-1,3,4,5-tetrahydro-6H-azepino[5,4,3-cd]indol-6-one, which route is developed via a key Sonogashira coupling reaction and a CuI-promoted indole formation.

SUMMARY OF THE INVENTION

In one embodiment, the present invention provides a method of preparing a compound of formula I

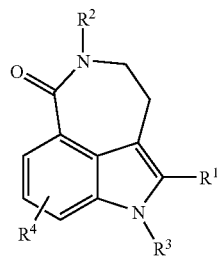

wherein R$^1$ is:
H;
cyano;
an optionally unsubstituted or substituted alkyl, alkenyl, alkynyl, cycloalkyl, heterocycloalkyl, aryl, or heteroaryl group; or
—C(O)—R$^5$, where R$^5$ is: H; an optionally unsubstituted or substituted alkyl, alkenyl, alkynyl, cycloalkyl, heterocycloalkyl, aryl, or heteroaryl group; or OR$^6$ or NR$^6$R$^7$, where R$^6$ and R$^7$ are each independently H or an optionally unsubstituted or substituted alkyl, alkenyl, alkynyl, cycloalkyl, heterocycloalkyl, aryl, or heteroaryl group;
R$^2$ is H or alkyl;
R$^3$ is H or alkyl;
R$^4$ is H, halogen or alkyl, the method comprising:
a) Sonogashira coupling of a compound of formula II, wherein X is halogen or CF$_3$SO$_2$—O—

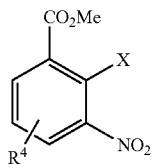

with a compound of formula III

to form a compound of formula IV;

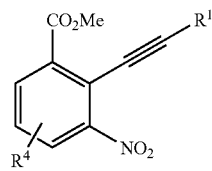

b) reducing the compound of formula IV to generate a compound of formula V;

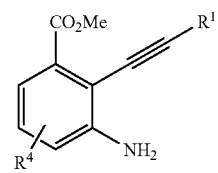

c) converting the compound of formula V into a compound of formula VI; and

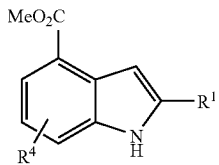

d) converting the compound of formula VI into the compound of formula I.

In another embodiment, the invention provides a method of preparing 8-fluoro-2-{4-[(methylamino)methyl]phenyl}-1,3,4,5-tetrahydro-6H-azepino[5,4,3-cd]indol-6-one, the method comprising Sonogashira coupling of a compound of formula VII, wherein X is halogen or CF$_3$SO$_2$—O—,

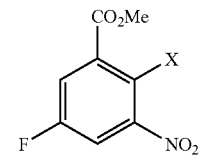

with (4-ethynyl-benzyl)-methyl-carbamic acid methyl ester to form 5-fluoro-2-{4-[(methoxycarbonyl-methyl-amino)-methyl]-phenylethynyl}-3-nitro-benzoic acid methyl ester.

In another embodiment, the invention provides a method of preparing 8-fluoro-2-{4-[(methylamino)methyl]phenyl}-1,3,4,5-tetrahydro-6H-azepino[5,4,3-cd]indol-6-one, the method comprising Sonogashira coupling of a compound of formula VII, wherein X is halogen or CF$_3$SO$_2$—O—,

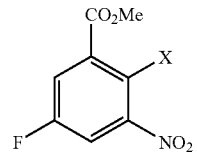

with (4-ethynyl-benzyl)-methyl-carbamic acid methyl ester to form 5-fluoro-2-{4-[(methoxycarbonyl-methyl-amino)-methyl]-phenylethynyl}-3-nitro-benzoic acid methyl ester; reducing 5-fluoro-2-{4-[(methoxycarbonyl-methyl-amino)-methyl]-phenylethynyl}-3-nitro-benzoic acid methyl ester into 3-amino-5-fluoro-2-{4-[(methoxycarbonyl-methyl-amino)-methyl]-phenylethynyl}-benzoic acid methyl ester; converting 3-amino-5-fluoro-2-{4-[(methoxycarbonyl-methyl-amino)-methyl]-phenylethynyl}-benzoic acid methyl ester into 6-fluoro-2-{4-[(methoxycarbonyl-methyl-amino)-methyl]-phenyl}-1H-indole-4-carboxylic acid methyl ester a CuI-promoted indole formation;

treating 6-fluoro-2-{4-[(methoxycarbonyl-methyl-amino)-methyl]-phenyl}-1H-indole-4-carboxylic acid methyl ester with N,N-dimethyl-2-nitroethylenamine to generate 6-fluoro-2-{4-[(methoxycarbonyl-methyl-amino)-methyl]-phenyl}-3-((E)-2-nitro-vinyl)-1H-indole-4-carboxylic acid methyl ester;

reducing 6-fluoro-2-{4-[(methoxycarbonyl-methyl-amino)-methyl]-phenyl}-3-((E)-2-nitro-vinyl)-1H-indole-4-carboxylic acid methyl ester into 6-fluoro-2-{4-[(methoxycarbonyl-methyl-amino)-methyl]-phenyl}-3-(2-nitro-ethyl)-1H-indole-4-carboxylic acid methyl ester;

hydrogenating 6-fluoro-2-{4-[(methoxycarbonyl-methyl-amino)-methyl]-phenyl}-3-(2-nitro-ethyl)-1H-indole-4-carboxylic acid methyl ester to produce [4-(8-fluoro-6-oxo-3,4,5,6-tetrahydro-1H-azepino[5,4,3-cd]indol-2-yl)-benzyl]-methyl-carbamic acid methyl ester; and deprotecting [4-(8-fluoro-6-oxo-3,4,5,6-tetrahydro-1H-azepino[5,4,3-cd]indol-2-yl)-benzyl]-methyl-carbamic acid methyl ester to produce 8-fluoro-2-{4-[(methylamino) methyl]phenyl}-1,3,4,5-tetrahydro-6H-azepino[5,4,3-cd] indol-6-one.

Definitions and Abbreviations

As used herein, the term "alkyl" means a branched- or straight-chained (linear) paraffinic hydrocarbon group (saturated aliphatic group) having from 1 to 10 carbon atoms in its chain, which may be generally represented by the formula C$_k$H$_{2k+1}$, where k is an integer of from 1 to 10. Examples of alkyl groups include methyl, ethyl, n-propyl, isopropyl, n-butyl, isobutyl, t-butyl, pentyl, n-pentyl, isopentyl, neopentyl, and hexyl, and the simple aliphatic isomers thereof. A "lower alkyl" is intended to mean an alkyl group having from 1 to 4 carbon atoms in its chain.

The term "alkenyl" means a branched- or straight-chained olefinic hydrocarbon group (unsaturated aliphatic group having one or more double bonds) containing 2 to 10 carbons in its chain. Exemplary alkenyls include ethenyl, 1-propenyl, 2-propenyl, 1-butenyl, 2-butenyl, isobutenyl, and the various isomeric pentenyls and hexenyls (including both cis and trans isomers).

The term "alkynyl" means a branched or straight-chained hydrocarbon group having one or more carbon-carbon triple bonds, and having from 2 to 10 carbon atoms in its chain. Exemplary alkynyls include ethynyl, propynyl, 1-butynyl, 2-butynyl, and 1-methyl-2-butynyl.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

The term "heterocycle" refers to a saturated, partially saturated, unsaturated, or aromatic, monocyclic or fused or non-fused polycyclic, ring structure having one or more heteroatoms selected from N, O, and S. Exemplary heterocycles include heterocycloalkyl, heteroaryl, and heterocycloalkyl-heteroaryl groups.

A "cycloalkyl group" is intended to mean a non-aromatic monovalent, monocyclic or fused polycyclic, ring structure having a total of from 3 to 18 carbon ring atoms (but no heteroatoms). Exemplary cycloalkyls include cyclopropyl, cyclobutyl, cyclopentyl, cyclopentenyl, cyclohexyl, cycloheptyl, adamantyl, phenanthrenyl, and like groups.

A "heterocycloalkyl group" is intended to mean a non-aromatic monovalent, monocyclic or fused polycyclic, ring structure having a total of from 3 to 18 ring atoms, including 1 to 5 heteroatoms selected from nitrogen, oxygen, and sulfur. Illustrative examples of heterocycloalkyl groups include pyrrolidinyl, tetrahydrofuryl, piperidinyl, piperazinyl, morpholinyl, thiomorpholinyl, aziridinyl, and like groups.

The term "aryl" means an aromatic monocyclic or fused polycyclic ring structure having a total of from 4 to 18, preferably 6 to 18, ring carbon atoms (no heteroatoms). Exemplary aryl groups include phenyl, naphthyl, anthracenyl, and the like.

A "heteroaryl group" is intended to mean an aromatic monovalent, monocyclic or fused polycyclic, ring structure having from 4 to 18, preferably 5 to 18, ring atoms, including from 1 to 5 heteroatoms selected from nitrogen, oxygen, and sulfur. Illustrative examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, and the like.

The term "optionally substituted" is intended to indicate that the specified group is unsubstituted or substituted by one or more suitable substituents, unless the optional substituents are expressly specified, in which case the term indicates that the group is unsubstituted or substituted with the specified substituents. Unless indicated otherwise (e.g., by indicating that a specified group is unsubstituted), the various groups defined above may be generally unsubstituted or substituted (i.e., they are optionally substituted) with one or more suitable substituents.

The term "substituent" or "suitable substituent" is intended to mean any substituent for a group that may be recognized or readily selected by the artisan, such as through routine testing, as being pharmaceutically suitable. Illustrative examples of suitable substituents include hydroxy, halogen (F, Cl, I, or Br), oxo, alkyl, acyl, sulfonyl, mercapto, nitro, alkylthio, alkoxy, cycloalkyl, heterocycloalkyl, aryl, heteroaryl, carboxy, amino (primary, secondary, or tertiary), carbamoyl, aryloxy, heteroaryloxy, arylthio, heteroarylthio, and the like (e.g., as illustrated by the exemplary compounds described herein). Suitable substituents are seen from the exemplary compounds that follow.

Preferred optional substituents for alkyl and aryl groups in the compounds of the invention include halogens and aryl groups. Especially preferred for substituted alkyl groups are perfluoro-substituted alkyls. Especially preferred optional substituents for aryl moieties include halogen, lower alkyl, —OH, —NO$_2$, —CN, —CO$_2$H, O-lower alkyl, aryl, —O-aryl, aryl-lower alkyl, —CO$_2$CH$_3$, —CONH$_2$, —OCH₂CONH₂, —NH₂, —SO₂NH₂, —OCHF₂, —CF₃, —OCF₃, and the like. Aryl moieties may also be optionally substituted by two substituents forming a bridge, for example —O—(CH₂)$_z$—O—, where z is an integer of 1, 2, or 3.

As used in the present application, "Et" means ethyl, "Ac" means acetyl, "Me" means methyl, "Ms" means methanesulfonyl (CH₃SO₂), "iPr" means isopropyl, "HATU" means 2-(7-Aza-1H-benzotriazole-1-yl)-1,1,3,3-tetramethyluronium hexafluorophosphate, "Ph" means phenyl, "Boc" means tert-butoxycarbonyl, "EtOAc" means ethyl acetate, "HOAc" means acetic acid, "NEt₃" or "Et₃N" means triethylamine, "Tf" means trifluoromethansulfonyl, "THF" means tetrahydrofuran, "DIC" means diisopropylcarbodiimide, "HOBt" means hydroxy benzotriazole, "MeOH" means methanol, "i-PrOAc" means isopropyl acetate, "KOAc" means potassium acetate, "DMSO" means dimethylsulfoxide, "AcCl" means acetyl chloride, "CDCl₃" means deuterated chloroform, "MTBE" means methyl t-butyl ether, "DMF" means dimethyl formamide, "Ac₂O" means acetic anhydride, "Me₃SOI" means trimethylsulfoxonium iodide, "DMAP" means 4-dimethylaminopyridine, "dppf" means diphenylphosphino ferrocene, "DME" means ethylene glycol dimethyl ether (1,2-dimethoxyethane), HOBT means 1-hydroxybenzotriazole, EDC means 1-ethyl-3-(3-dimethylaminopropyl)-carbodiimide.

DETAILED DESCRIPTION OF THE INVENTION

The present invention provides a new and convergent route to the tricyclic inhibitors of poly(ADP-ribose) polymerase (PARP), which inhibitors are disclosed in the above-mentioned U.S. Pat. No. 6,495,541. For illustrative purposes only, the method of the present invention is demonstrated by the example of the method of preparing 8-fluoro-2-{4-[(methylamino)methyl]phenyl}-1,3,4,5-tetrahydro-6H-azepino[5,4,3-cd]indol-6-one. The reagents and conditions of the reactions described herein, are merely illustrative of the wide variety of starting materials, their amounts and conditions which may be suitably employed in the present invention as would be appreciated by those skilled in the art, and are not intended to be limiting in any way.

The method of the present invention comprises preparation of 8-fluoro-2-{4-[(methylamino)methyl]phenyl}-1,3,4,5-tetrahydro-6H-azepino[5,4,3-cd]indol-6-one (compound 15) via a key Sonogashira coupling reaction and a CuI-promoted indole formation according to Scheme 1.

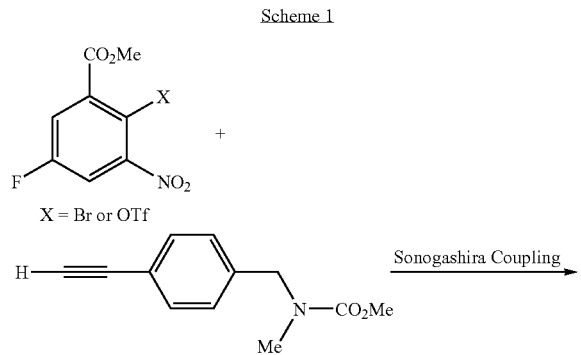

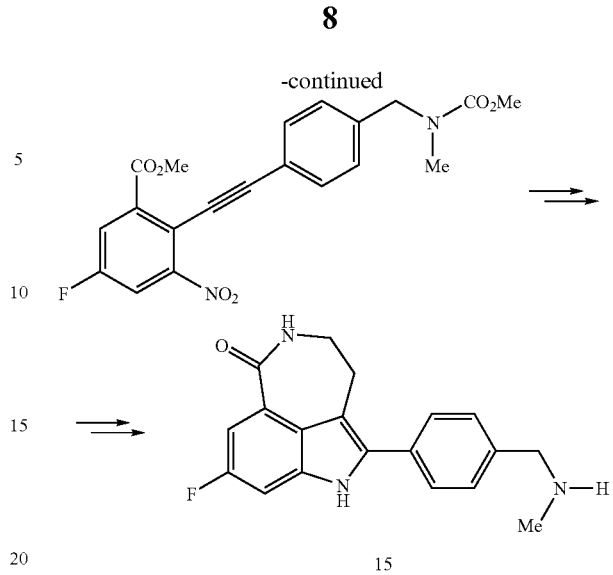

I. Preparation of Alkyne 5 and Triflate Precursor 8 for Sonogashira Coupling

The synthesis of alkyne 5 is shown in Scheme 2. Aldehyde 2, though available from Aldrich, is expensive, therefore it can be more economical to prepare it from relatively inexpensive 4-bromobenzaldehyde 1 following a literature procedure as described in Thorand, S. and Krause, N. *J. Org. Chem.* 1998, 63, 8551. Next, reductive amination of aldehyde 2 with methylamine can afford amine 3, which can be subsequently protected to give methyl carbamate 4. Removal of the trimethylsilyl group (TMS) under basic conditions can yield 5 in 90% yield.

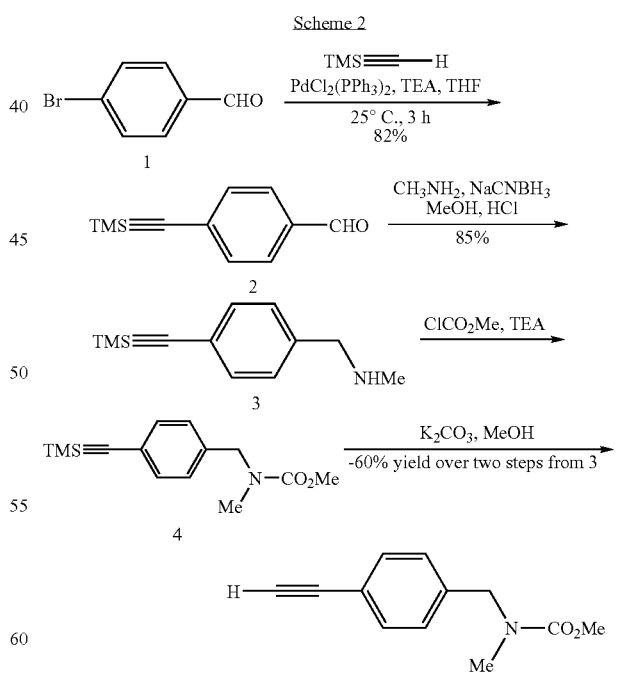

The triflate precursor 8 can be prepared via nitration of 5-fluorosalicylic acid 6 using tetramethylamonium nitrate and trifluoroacetic acid anhydride employing standard conditions (Scheme 3). The desired product 8 can be obtained regiospecifically as a yellow solid after crystallization from CH₃CN/H₂O in 63% yield.

Scheme 8

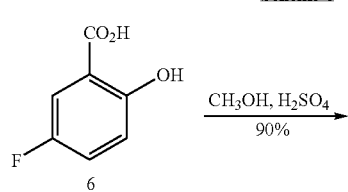

II. Synthesis of Indole Intermediate 11

As indicated in Scheme 4, although the triflate 16 could be isolated, it is more advantageous to prepare it in situ.

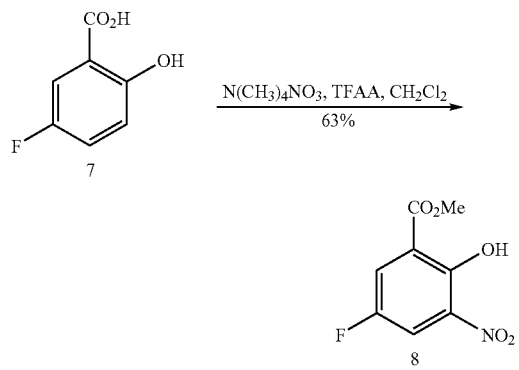

The formation of triflate 16 and its coupling with the alkyne 5 can be carried out in a one-pot fashion to afford intermediate 9. The preferred conditions for this coupling are as follows: a CH₃CN-solution containing alkyne 5 and the pre-formed triflate 16 is added to a solution containing 2% PdCl₂(PPh₃)₂ in CH₃CN at 60° C. Under these conditions, the dimer 17 is determined to be the major by-product. Further, the addition of co-catalyst CuI is found to be detrimental since it promoted more dimer formation. After work-up, crude product 9 can be reduced with iron powder. Addition of a few drops of concentrated HCl is very helpful in activating iron powder. Subsequent cyclization of crude compound 10 to indole 11 can be effected with a catalytic amount of CuI in DMF. Indole 11 can be obtained in 51% yield over 3 steps after trituration with methylene chloride/hexanes in order to remove by-product 17.

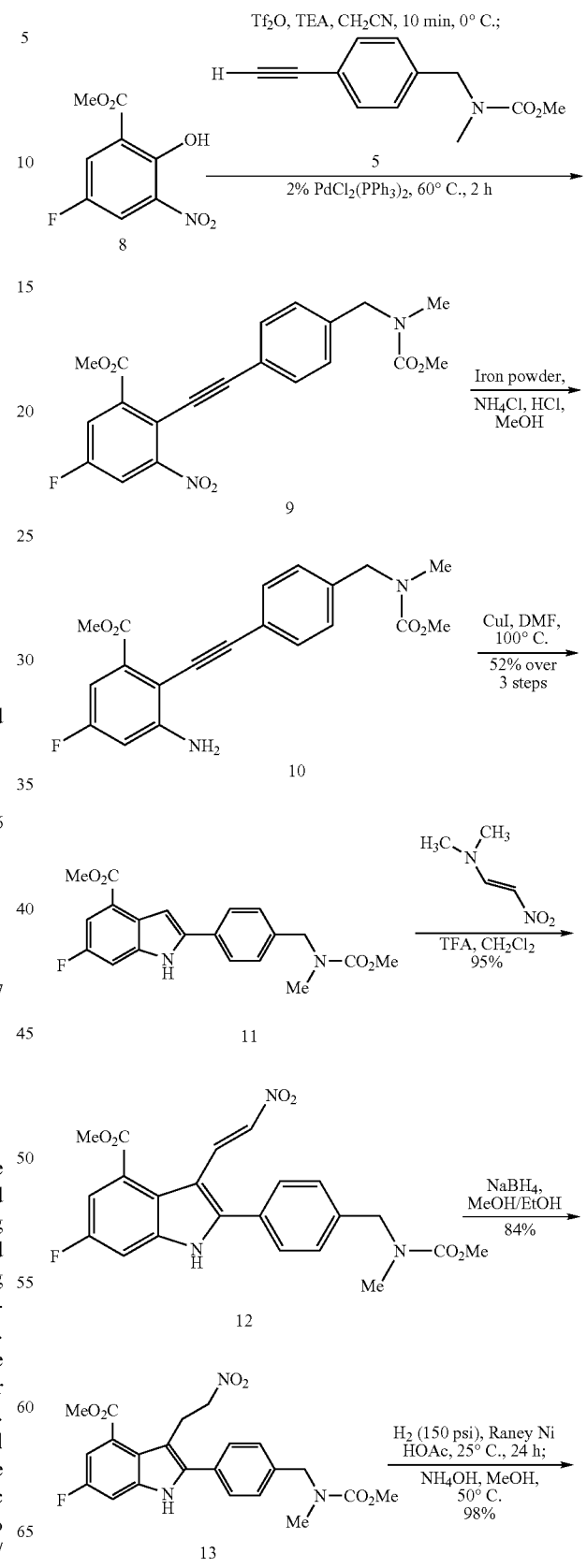

-continued

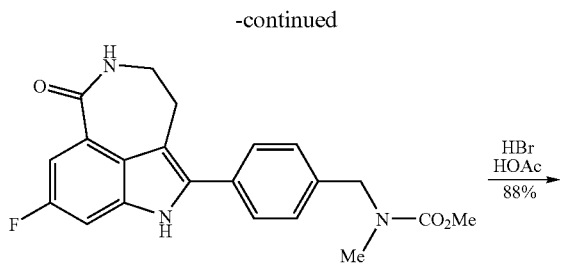

14

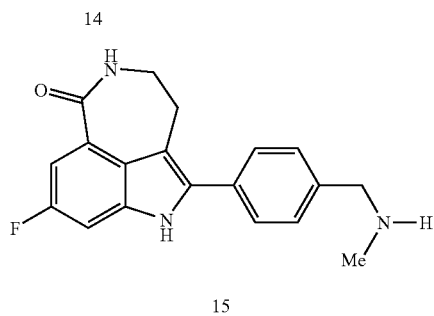

15

III. Conversion of Indole Intermediate 11 into Target Compound 15

Treatment of indole 11 with N,N-dimethyl-2-nitroethylenamine (Mahboobi, S.; Elbler, E.; Roller, M.; Kumar, S.; Popp, A. *J. Org. Chem.* 1999, 64; 4697) in TFA/CH$_2$Cl$_2$ furnishes nitroalkene 12 (Scheme 4). Nitroalkene 12 can be then reduced with sodium borohydride in 9:1 EtOH/MeOH mixture to nitroalkane 13 in 84% yield. Due to the poor solubility of 12 and 13 in EtOH, a high volume of solvent is necessary to ensure complete conversion. Hydrogenation of 13 to lactam 14 using Pd/C or Pt/C under neutral condition affords N-hydroxy lactam 18 as a major side product. However, when hydrogenation is carried out under acidic conditions with Pd/C or Pt/C, the formation of 18 is suppressed, but it induces cleavage of C—N bond in 13 to afford 19 as another major side product. Since Raney-Ni does not promote cleavage of C—N bonds, hydrogenation reactions under Raney-Ni mediated conditions should be screened. Surprisingly, it was found that hydrogenation of 13 employing Raney-Ni works well under either neutral or acidic conditions. Thus, nitroalkane 13, on reduction with Raney-Ni in acetic acid, affords the corresponding amine acetate which upon treatment with base cyclized to 14 in 96% yield on 20 g scale without any side products.

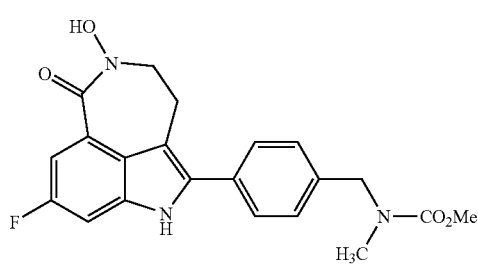

18

-continued

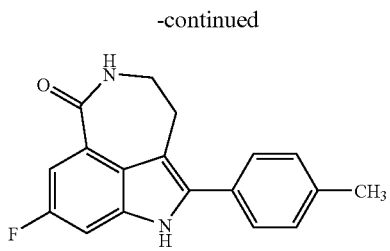

19

Finally, the carbamate group in 14 is readily deprotected by HBr/acetic acid at ambient temperature to provide 15. Initial attempts to remove carbamate group with alkaline hydrolysis, for example, 8 N KOH in EtOH at 80° C. lead to an undesired cleavage of the lactam ring in 15. Although methyl carbamates can also be cleaved by trimethylsilyl iodide, the formation of methyl iodide byproduct raises a safety concern and makes this method less attractive. On the other hand, the toxic methyl bromide generated during cleavage with HBr/acetic acid can be efficiently trapped with an ethanolamine scrubber system as described in Hettenbach, K.; Am Ende, D. J.; Leeman, K.; Dias, E.; Kasthurikrishnan, N.; Brenek, S. J.; Ahlijanian, P. *Organic Process Research & Development,* 2002, 6, 407. In this manner, a 20 g lot of target compound 15 is prepared which is identical to an authentic sample synthesized by a previous route.

The disclosures of all cited references are incorporated herein by reference in their entirety.

EXAMPLES

The examples and preparations provided below further illustrate and exemplify the methods of the present invention. It is to be understood that the scope of the present invention is not limited in any way by the scope of the following examples.

Example 1

Synthesis of 4-trimethylsilanylethynyl-benzaldehyde (2)

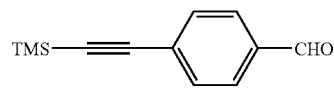

4-Bromobenzaldehyde (1) (185 g, 1.0 mole) was dissolved in THF (1 L) followed by addition of copper (I) iodide (7.6 g, 0.04 mol), dicholobis(triphenylphospine) palladium (II) (14.02 g, 0.02 mol) and triethylamine (151.5 g, 1.5 mol). Ethynyltrimethylsilane (109.1 g, 1.11 mol) was added from addition funnel as a solution in THF (0.2 L). The reaction was stirred at 30° C. for 30 min and then at 25° C. for 20 hours. Analysis by HPLC indicated the completion of the reaction. THF was removed and the residue was treated with hexane (1.8 L). The solid was removed by filtration and the filter cake washed with hexane (0.3 L). The combined hexane solution was washed with water (2×0.5 L). Hexane was removed in a rotovap. The residue was dissolved in EtOH (0.5 L) at 50° C. The solution was then slowly cooled to 16° C. and was stirred for 30 minutes. Product started to crystallize. The mixture was further cooled to 5° C. 1:1 of EtOH/H$_2$O (0.24 L) was added slowly. The mixture was stirred at 5° C. for 30 minutes. Solid was collected by filtration, washed with 4:1 of EtOH/H$_2$O (0.2 L) and dried to provide 137.0 g of product. The mother liquor was concentrated to dryness. The residue was partitioned between hexane (0.5 L) and brine (0.25 L). Hexane layer was separated and concentrated to dryness. The residue was crystallized from hexane (40 ml) and further recrystallized from 4:1 of EtOH/H$_2$O (0.1 L) to provide second crop of aldehyde 2 (27.0 g). The combined yield for aldehyde 2 was 81%. $^1$H NMR (300 MHz, CDCl$_3$) δ 0.081 (s, 9H), 7.41 (d, 2H, J=8.1 Hz), 7.63 (d, 2H, J=8.4 Hz), 9.81 (s, 1H).

Example 2

Synthesis of methyl-(4-trimethylsilanylethynyl-benzyl)-amine (3)

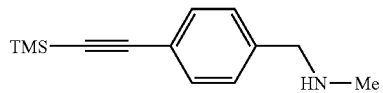

Methyl amine (8 M in MeOH, 135 ml) and methyl amine hydrochloride (44.0 g, 0.65 mol) were dissolved in methanol (900 ml). Aldehyde 2 (44.0 g, 0.22 mol) was added and stirred at room temperature for 30 min. Sodium cynoborohydride (17.42 g, 0.28 mol) was then added. After addition was complete, hydrochloride methanolic solution was added to adjust the pH to 5 while the temperature was held at ~30° C. The reaction was stirred for 2 hours. The pH of the reaction mixture was maintained between 4 and 6 by addition of hydrochloride solution in MeOH. The reaction solvent was removed. The residue was taken up with water (400 ml) and brine (50 ml). The mixture was extracted with methylene chloride (2×300 ml). The combined organic solution was concentrated to dryness to afford the crude product (40.6 g, ~85% yield), which was used directly in the next step without further purification. $^1$H NMR (300 MHz, CDCl$_3$) δ 0.254 (s, 9H), 2.434 (s, 3H), 3.736 (s, 2H), 7.25 (d, 2H, J=9 Hz), 7.43 (d, 2H, J=9 Hz). Exact mass calculated for C$_{13}$H$_{20}$NSi: 218.1365. Found: 218.1357.

Example 3

Synthesis of methyl-(4-trimethylsilanylethynyl-benzyl)-carbamic acid methyl ester (4)

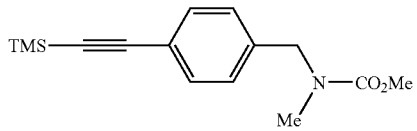

Amine 3 (90.0 g, ~0.41 mol) was dissolved in methylene chloride (810 ml). Triethylamine (66.6 g, 0.66 mol) was added and the solution was cooled to 5° C. Methyl chloroformate (47.0 g, 0.50 mol) in methylene chloride (100 ml) was then added slowly and the reaction temperature was maintained between 10° C. and 14° C. After addition was complete, the reaction solution was stirred at room temperature for 12 hours. Water (540 ml) was added. Aqueous phase was separated. Organic phase was concentrated to dryness to afford crude compound 4. The crude product was used in the next step without further purification. $^1$H NMR (300 MHz, CDCl$_3$) δ 0.279 (s, 9H), 2.86 (d, br, 3H), 3.774 (s, 3H), 4.484 (s, br, 2H), 7.190 (s, br, 2H), 7.46 (d, 2H, J=8.10 Hz).

Example 4

Synthesis of (4-ethynyl-benzyl)-methyl-carbamic acid methyl ester (5)

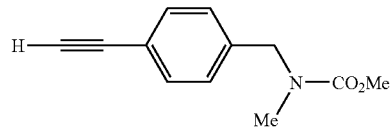

Carbamate 4 from step 3 was dissolved in methanol (630 ml). Potassium carbonate (10.5 g, 0.08 mol) was added. The reaction mixture was stirred at room temperature for 1 hour. TLC analysis indicated the completion of the reaction. White solid was filtered off. Methanol was removed by distillation under reduced pressure to afford yellow oil. The oil was further purified by column chromatography (silica gel, hexane/EtOAc) to yield 50.2 g of compound 5 (~60% yield over two steps from amine 3). $^1$H NMR (300 MHz, CDCl$_3$) δ 2.85 (d, br, 3H), 3.068 (s, 1H), 3.744 (s, 3H), 4.468 (s, br, 2H), 7.195 (s, br, 2H), 7.46 (d, 2H, J=8.1 Hz). Exact mass calculated for C$_{12}$H$_{14}$NO$_2$: 204.1025. Found: 204.1022.

Example 5

Synthesis of 5-fluorosalicylic acid methyl ester (7)

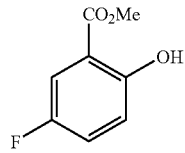

5-Fluorosalicylic acid (272.6 g, 1.74 mol) was dissolved in methanol (1.3 L) to form a clear solution. Concentrated sulfuric acid (50 ml) was slowly added to the methanol solution with vigorous stirring. The solution was heated to reflux for 4 hours. Trimethyl orthoformate (200 ml) was added slowly to the reaction solution. 300 ml of solvents (methyl formate and methanol) was distilled off. The remaining reaction solution was heated at 66° C. (refluxing temperature) for 16 hours. HPLC analysis indicated that the reaction was complete. Reaction solution was cooled to ambient temperature. Solvent was removed under reduced pressure. The residue was partitioned between water (140 ml) and methylene chloride (220 ml). Organic layer was separated. Aqueous layer was extracted with methylene chloride (3×220 ml). The combined organic layer was washed with water (270 ml), brine (270 ml) and dried with MgSO$_4$. The organic solution was concentrated to dryness to afford crude product (293.8 g). This crude material was used in the next step without further purification. $^1$H NMR (300 MHz, CDCl$_3$) δ 3.96 (s, 3H), 6.94 (dd, 1H, J=4.5 Hz and J=9.0 Hz), 7.19 (m, 1H), 7.50 (dd, 1H, J=3.3 Hz and J=8.7 Hz), 10.508 (s, 1H).

Example 6

Synthesis of 5-fluoro-2-hydroxy-3-nitro-benzoic acid methyl ester (8)

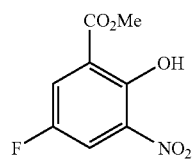

Tetramethylammonium nitrate (98.4 g, 0.72 mol) was suspended in methylene chloride (800 ml). Triflouroacetic anhydride (180.3 g, 0.857 mol) was added to the mixture with stirring. The mixture was cooled to 8° C. The solution of ester 7 (106 g, 0.624 mol) in $CH_2Cl_2$ (150 ml) was then added slowly to the reaction flask over 25 minutes while the temperature was maintained between 5° C. and 10° C. Reaction mixture was stirred at 8° C. for additional 40 minutes after addition was complete. Saturated aqueous sodium bicarbonate (500 ml) was added slowly to quench the reaction. Organic layer was separated, washed with water (2×500 ml) and concentrated to dryness to afford crude solid. The solid was dissolved in acetonitrile (300 ml) at 55° C. Water (100 ml) was added slowly to the acetonitrile solution with stirring and solid precipitated out. The suspension was cooled to 18° C. and stirred at this temperature for 30 minutes. It was then cooled to 3° C. and stirred at this temperature for 30 minutes. The solid was collected by filtration. The filter cake was washed with cold solvent $CH_3CN/H_2O$ (2/1, 100 ml) and dried to afford 78.49 g of light yellow product (57% yield over two steps). $^1$H NMR (300 MHz, $CDCl_3$) δ 4.035 (s, 3H), 7.88 (dd, 1H, J=3.6 Hz and J=9.0 Hz), 7.94 (dd, 1H, J=3.3 Hz and J=7.5 Hz), 11.71 (s, 1H). Exact mass calculated for $C_8H_5FNO_5$: 214.0152. Found: 214.0141.

Example 7

Synthesis of 5-Fluoro-2-{4-[(methoxycarbonyl-methyl-amino)-methyl]-phenylethynyl}-3-nitro-benzoic acid methyl ester (9)

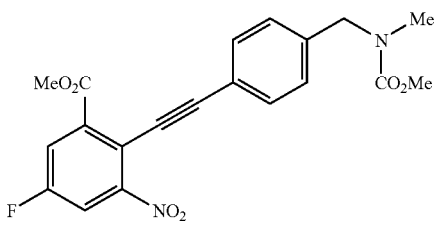

The nitro compound 8 (47.87 g, 0.223 mol) was dissolved in acetonitrile (240 ml) and cooled to −8° C. Triethylamine (33.8 g, 0.334 mol) was added. A clear dark solution was formed. Triflic anhydride (69.17 g, 0.245 mol) was added slowly and the reaction temperature was maintained at −10° C. 10 minutes after addition was complete, TLC analysis indicate the completion of triflate formation. Cooling bath was removed. Alkyne 5 (47.46 g, 0.234 mol) was added. The solution was degassed 3 times by evacuating the flask and backfilling it with nitrogen. The solution was then transferred into an addition funnel. Into a separate reaction flask was added acetonitrile (240 ml) and triethylamine (22.5 g, 0.223 mol). The solution was degassed 3 times by exposing the reaction flask to vacuum and nitrogen alternatively. Dichlorobis(triphenylphosphine) palladium (II) (3.13 g, 0.0045 mol) was added to the solution and the solution was degassed again 3 times. This solution was heated to 65° C. under protection of nitrogen. Once the temperature reached 65° C., one quarter of the solution of alkyne 5 and triflate in addition funnel was quickly added to the reaction flask. The remaining solution in addition funnel was added over 30 minutes at 65° C. After the addition was complete, the reaction solution was stirred at 65° C. for 2 hours. HPLC analysis indicated the reaction was complete. Reaction mixture was cooled to room temperature. Solvent was removed under reduced pressure. The residue was dissolved in ethyl acetate (500 ml) and washed with water (300 ml). The aqueous phase was separated and back extracted with ethyl acetate (200 ml). The combined organic solution was washed with water (200 ml). It was then concentrated to dryness to provide a dark oil residue (140 g). This crude product was used in the next step without further purification. $^1$H NMR (300 MHz, $CDCl_3$) δ 2.87 (d, br, 3H), 3.755 (s, 3H), 4.011 (s, 3H), 4.50 (s, br, 2H), 7.21 (s, br, 2H), 7.55 (d, 2H, J=9 Hz), 7.80 (dd, 1H, J=2.7 Hz and J=7.2 Hz), 7.86 (dd, 1H, J=2.7 Hz and J=8.1 Hz).

Example 8

Synthesis of 3-amino-5-fluoro-2-{4-[(methoxycarbonyl-methyl-amino)-methyl]-phenylethynyl}-benzoic acid methyl ester (10)

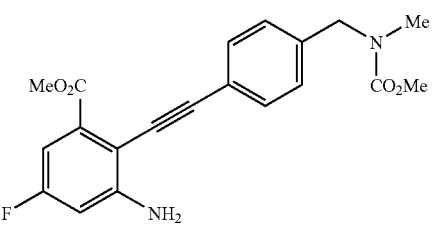

The crude compound 9 (140 g) was dissolved in methanol (1.05 L). Iron powder (325 mesh, 76.2 g, 1.36 mol) was added followed by addition of saturated aqueous ammonium chloride (210 ml). The solution was heated to 65° C. Aqueous hydrochloric acid (16 wt %, 32 ml) was added. The reaction was heated at 65° C. for 2 hours. HPLC analysis indicated the completion of the reaction. The reaction mixture was cooled to room temperature. Solid was removed by filtration. The filter cake was washed with methanol (2 L). The combined methanol solution was concentrated to dryness. The residue was partitioned between ethyl acetate (800 ml) and diluted aqueous hydrochloric solution (0.5 M, 300 ml). Organic layer was separated. Aqueous layer was extracted with ethyl acetate (3×200 ml). The combined organic solution was washed with brine (200 ml). The solution was then concentrated to dryness to afford 122.8 g of crude product as dark oil. This crude product was used in the next step without further purification. $^1$H NMR (300 MHz, $CDCl_3$) δ 2.87 (d, br, 3H), 3.491 (s, 3H), 3.932 (s, 3H), 4.486 (s, br, 2H), 6.60 (dd, 1H, J=2.7 Hz and J=9.9 Hz), 7.04 (dd, 1H, J=2.4 Hz and J=9.0 Hz), 7.237 (s, br, 2H), 7.52 (d, 2H, J=8.1 Hz).

Example 9

Synthesis of 6-fluoro-2-{4-[(methoxycarbonyl-methyl-amino)-methyl]-phenyl}-1H-indole-4-carboxylic acid methyl ester (11)

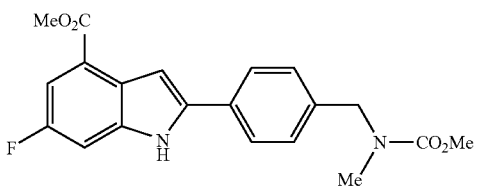

Crude compound 10 (114.37 g, ~0.309 mol) was dissolved in DMF (1.5 L). Copper (I) iodide (99.9999% purity, 5.8 g, 0.0309 mol) was added. The reaction mixture was degassed 4 times by exposing the reaction flask to vacuum and nitrogen alternatively. The reaction mixture was then heated at 100° C. for 44 hours under protection of nitrogen. HPLC analysis indicated the disappearance of starting material. Reaction mixture was cooled to ambient temperature. Solvent was removed under reduced pressure (9 mbar) at 35° C. The black residue was dissolved in $CH_2Cl_2$ (0.15 L). The mixture was passed through a Celite pad. The organic solution was then passed through a silica gel pad (300 g of silica gel). $CH_2Cl_2$ (2.3 L) was used to elute compound from silica gel pad. Organic solution was concentrated to dryness. The residue was dissolved $CH_2Cl_2$ (0.15 L). Hexane (1 L) was added slowly to the solution with stirring. The precipitated product was collected by filtration, washed with EtOAc (0.2 L) and dried to afford 31.34 g of product. The EtOAc wash was combined with mother liquor. The solution was concentrated to dryness. The residue was dissolved in $CH_2Cl_2$ (0.15 L). The solution was then passed through a pad of silica gel (300 g). The silica gel pad was washed with $CH_2Cl_2$ to elute out the compound. The organic solution was concentrated to dryness. The residue was dissolved $CH_2Cl_2$ (0.07 L). Heptane (0.22 L) was added to precipitate out product. Solid was collected, washed with 1:3 of $CH_2Cl_2$/heptane (0.06 L) and dried to provide additional 27.51 g of product. The combined product weighed 58.85 g, which translated to 51% yield over 3 steps from compound 8. $^1H$ NMR (300 MHz, $CDCl_3$) δ 2.896 (s, 3H), 3.779 (s, 3H), 4.006 (s, 3H), 4.516 (s, 2H), 7.31 (dd, 2H, J=1.5 Hz and J=8.7 Hz), 7.429 (s, 1H), 7.65 (m, 3H), 9.17 (d, br, 1H). Exact mass calculated for $C_{20}H_{20}FN_2O_4$: 371.1407. Found: 371.1418.

Example 10

Synthesis of 6-Fluoro-2-{4-[(methoxycarbonyl-methyl-amino)-methyl]-phenyl}-3-((E)-2-nitro-vinyl)-1H-indole-4-carboxylic acid methyl ester (12)

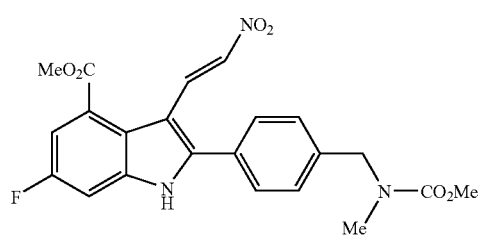

Trifluoroacetic acid (0.14 L) was cooled to 5° C. 1-N,N-dimethylamino-2-nitro ethylene (15.0 g, 0.129 mol) was added to TFA in portions at 5-8° C. A clear solution was formed. Indole 11 was added in several portions. $CH_2Cl_2$ (0.02 L) was then added. The reaction solution was stirred at ambient temperature for 44 hours. TLC analysis indicated that the reaction was complete. Solvent was removed under reduced pressure at 23° C. (47 mbar). The residue was poured slowly into a flask containing $CH_2Cl_2$ (0.4 L) and saturated aqueous $NaHCO_3$ (0.5 L). The final pH for the aqueous phase was 5.0. Organic phase was separated. Aqueous phase was extracted with $CH_2Cl_2$ (2×100 ml). The organic solution was combined and concentrated in a rotovap until solid crashed out. Heptane (0.2 L) was added to the $CH_2Cl_2$ suspension and the mixture was stirred for 30 minutes. Solid was collected, washed with 1:4 of $CH_2Cl_2$/heptane (100 ml) and dried in air to afford 49.18 g of product (95% yield). $^1H$ NMR (300 MHz, DMSO-$d_6$) δ 2.88 (s, 3H), 3.661 (s, 3H), 3.920 (s, 3H), 4.554 (s, 2H), 6.86 (d, 1H, J=13.5 Hz), 7.46 (d, 2H, J=7.5 Hz), 7.52 (d, 2H, J=9.3 Hz), 7.65 (d, 2H, J=8.1 Hz), 8.69 (d, 1H, J=13.5 Hz), 12.895 (s, br, 1H). Exact mass calculated for $C_{22}H_{21}FN_3O_6$: 442.1414. Found: 442.1420.

Example 11

Synthesis of 6-fluoro-2-{4-[(methoxycarbonyl-methyl-amino)-methyl]-phenyl}-3-(2-nitro-ethyl)-1H-indole-4-carboxylic acid methyl ester (13)

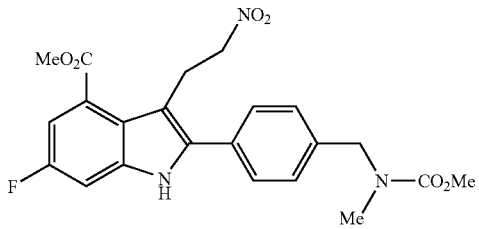

EtOH (900 ml) and MeOH (90 ml) were added to a 2 L flask. Powdered sodium borohydride (20.5 g, 0.55 mol) was then added. The suspension was cooled to 15° C. Nitroalkene 12 (49.0 g, 0.11 mol) was added in portions over 45 minutes while the temperature was maintained at ~15° C. After addition was complete, additional EtOH (800 ml) was added. The reaction mixture was stirred for 15 minutes. TLC analysis indicated the completion of the reaction. A mixture of acetic acid (40 ml) and water (40 ml) was added slowly to quench the excess of sodium borohydride. A reddish suspension was obtained. Solvent was removed in a rotovap. The residue was partitioned between EtOAc (600 ml) and water (300 ml). Aqueous phase was separated. The solid in organic layer was collected by filtration and dried to afford 21.94 g of product 13 (45% yield). The organic filtrate was concentrated to dryness. The residue was then reslurried with EtOAC (70 ml)/heptane (200 ml). The solid was collected by filtration and dried to afford second crop of product (21.74 g, 44% yield). The combined yield for this step is 89%. $^1H$ NMR (300 MHz, DMSO-$d_6$) δ 2.87 (s, 3H), 3.584 (t, 2H, J=7.8 Hz), 3.661 (s, 3H), 3.903 (s, 3H), 4.519 (s, 2H), 4.607 (t, 2H, J=7.8 Hz), 7.41 (m, 4H), 7.58 (d, 2H, J=8.10 Hz), 12.0 (s, br, 1H). Exact mass calculated for $C_{22}H_{23}FN_3O_6$: 444.1571. Found: 444.1559.

Example 12

Synthesis of [4-(8-Fluoro-6-oxo-3,4,5,6-tetrahydro-1H-azepino[5,4,3-cd]indol-2-yl)-benzyl]-methyl-carbamic acid methyl ester (14)

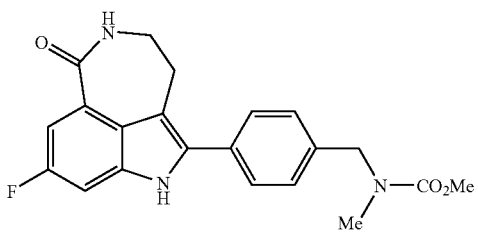

Raney nickel (30 ml, A-5000 from Active Metals) was washed with water (2×50 ml), MeOH (2×50 ml) and HOAc (50 ml). It was then mixed with HOAC (400 ml) and transferred to a 2 L hydrogenator. Nitro compound 13 (19.33 g, 0.044 mol) was added. The suspension was hydrogenated at 150 psi at ambient temperature for 20 hours. HPLC analysis indicated the starting material 13 disappeared. Catalyst was filtered off and the filter cake was washed with EtOH (200 ml). (Caution: Raney nickel may ignite in air. Never let the filter cake run dry). EtOH wash was combined with the filtrate. The solution was concentrated to dryness in a rotovap to give a green residue. The green residue was dissolved in MeOH (200 ml). Ammonium hydroxide (40 ml) was added to adjust the pH of the solution to ~10. The solution was then heated at 45° C. for 8 hours to cyclize the amine intermediate to lactam 14. White solid precipitated out over the course of cyclization. HPLC analysis indicated the completion of the reaction. The suspension was cooled to room temperature. The white solid was collected by filtration, washed with MeOH (20 ml) and dried in air to afford 8.9 g of product (98% yield). $^1$H NMR (300 MHz, DMSO-$d_6$) δ 2.85 (s, 3H), 3.05 (m, 2H), 3.39 (m, 2H), 3.66 (s, 3H), 4.486 (s, 2H), 7.39 (m, 4H), 7.76 (d, 2H, J=8.10 Hz), 8.24 (t, 1H, J=5.7 Hz), 11.66 (s, 1H). Exact mass calculated for $C_{21}H_{21}FN_3O_3$: 382.1567. Found: 382.1552.

Example 13

Synthesis of 8-Fluoro-2-(4-methylaminomethyl-phenyl)-1,3,4,5-tetrahydro-azepino[5,4,3-cd]indol-6-one (15)

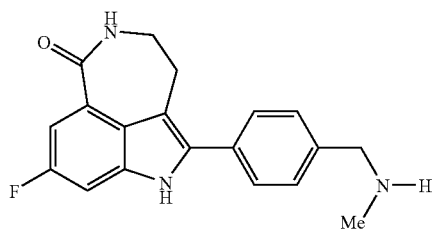

Lactam 14 (14.42 g, 0.038 mol) was dissolved in hydrobromic acid in acetic acid (30%-32%, 140 ml). The reaction solution was stirred for 46 hours at room temperature in a 500 ml flask that was connected to an ethanolamine scrubber system. HPLC analysis indicated the completion of the reaction. Ice (30 g) was added to the reaction solution followed by addition of aqueous NaOH (327 ml, 10 M, 3.27 mol) while the temperature was maintained between 25° C. and 35° C. When addition of NaOH was complete, the pH was 10. The resulting solid was collected by filtration, washed with water (2×50 ml). The filter cake was then suspended in water (125 ml) and stirred for 2 hours. The solid was collected by filtration, washed with water (2×25 ml) and dried to afford 10.76 g of product (88% yield). $^1$H NMR (300 MHz, DMSO-$d_6$) δ 2.577 (s, 3H), 3.053 (m, 2H), 3.406 (m, 2H), 4.159 (s, 2H), 7.36 (dd, 1H, J=2.4 Hz and J=9.3 Hz), 7.44 (dd, 1H, J=2.4 Hz and J=11.1 Hz), 7.63 (d, 2H, J=8.1 Hz), 7.70 (d, 2H, J=8.1 Hz), 8.265 (t, 1H, J=5.7 Hz), 11.77 (s, 1H). Exact mass calculated for $C_{19}H_{19}FN_3O$: 324.1512. Found: 324.1497.

We claim:

1. A method of preparing a compound of formula I

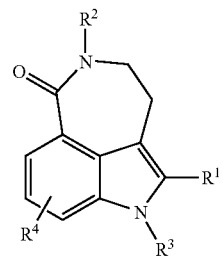

wherein $R^1$ is:
H;
cyano;
an optionally unsubstituted or substituted alkyl, alkenyl, alkynyl, cycloalkyl, heterocycloalkyl, aryl, or heteroaryl group; or
—C(O)—$R^5$, where $R^5$ is: H; an optionally unsubstituted or substituted alkyl, alkenyl, alkynyl, cycloalkyl, heterocycloalkyl, aryl, or heteroaryl group; or $OR^6$ or $NR^6R^7$, where $R^6$ and $R^7$ are each independently H or an optionally unsubstituted or substituted alkyl, alkenyl, alkynyl, cycloalkyl, heterocycloalkyl, aryl, or heteroaryl group;

$R^2$ is H;
$R^3$ is H or alkyl;
$R^4$ is H, halogen or alkyl, the method comprising:
a) Sonogashira coupling of a compound of formula II, wherein X is halogen or $CF_3SO_2$—O—

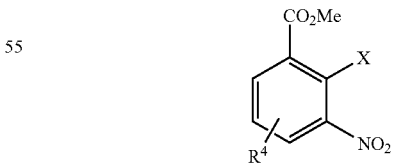

with a compound of formula III

to form a compound of formula IV

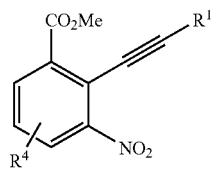

b) reducing the compound of formula IV to generate a compound of formula V;

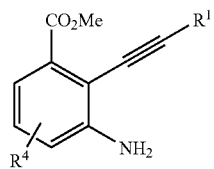

c) converting the compound of formula V into a compound of formula VI;

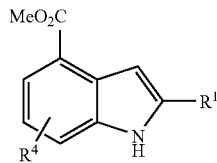

d) treating the compound of formula VI with N,N-dimethyl-2-nitroethylenamine to form a compound of formula VII

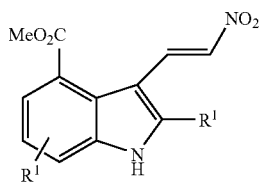

e) reducing the compound of formula VII to form a compound of formula VIII

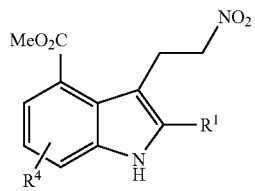

f) converting the compound of formula VIII by reduction with Raney-Ni and subsequent cyclization with base into the compound of formula I.

2. The method of claim 1, wherein the step c) comprises a CuI-promoted indole formation.

3. A method of preparing 8-fluoro-2-{4-[(methylamino)methyl]phenyl}-1,3,4,5-tetrahydro-6H-azepino[5,4,3-cd]indol-6-one, the method comprising Sonogashira coupling of a compound of formula IX, wherein X is $CF_3SO_2$—O— or halogen,

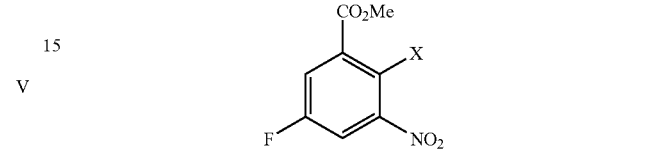

with (4-ethynyl-benzyl)-methyl-carbamic acid methyl ester to form 5-fluoro-2-{4-[(methoxycarbonyl-methyl-amino)-methyl]-phenylethynyl}-3-nitro-benzoic acid methyl ester.

4. The method of claim 3, wherein X is $CF_3SO_2$—O—.

5. The method of claim 3, wherein X is bromine.

6. The method of claim 3 further comprising:
a) reducing 5-fluoro-2-{4-[(methoxycarbonyl-methyl-amino)-methyl]-phenylethynyl}-3-nitro-benzoic acid methyl ester into 3-amino-5-fluoro-2-{4-[(methoxycarbonyl-methyl-amino)-methyl]-phenylethynyl}-benzoic acid methyl ester;
b) converting 3-amino-5-fluoro-2-{4-[(methoxycarbonyl-methyl-amino)-methyl]-phenylethynyl}-benzoic acid methyl ester into 6-fluoro-2-{4-[(methoxycarbonyl-methyl-amino)-methyl]-phenyl}-1H-indole-4-carboxylic acid methyl ester;
c) treating 6-fluoro-2-{4-[(methoxycarbonyl-methyl-amino)-methyl]-phenyl}-1H-indole-4-carboxylic acid methyl ester with N,N-dimethyl-2-nitroethylenamine to generate 6-fluoro-2-{4-[(methoxycarbonyl-methyl-amino)-methyl]-phenyl}-3-((E)-2-nitro-vinyl)-1H-indole-4-carboxylic acid methyl ester;
d) reducing 6-fluoro-2-{4-[(methoxycarbonyl-methyl-amino)-methyl]-phenyl}-3-((E)-2-nitro-vinyl)-1H-indole-4-carboxylic acid methyl ester into 6-fluoro-2-{4-[(methoxycarbonyl-methyl-amino)-methyl]-phenyl}-3-(2-nitro-ethyl)-1H-indole-4-carboxylic acid methyl ester;
e) converting 6-fluoro-2-{4-[(methoxycarbonyl-methyl-amino)-methyl]-phenyl}-3-(2-nitro-ethyl)-1H-indole-4-carboxylic acid methyl ester into [4-(8-fluoro-6-oxo-3,4,5,6-tetrahydro-1H-azepino[5,4,3-cd]indol-2-yl)-benzyl]-methyl-carbamic acid methyl ester; and
f) deprotecting [4-(8-fluoro-6-oxo-3,4,5,6-tetrahydro-1H-azepino[5,4,3-cd]indol-2-yl)-benzyl]-methyl-carbamic acid methyl ester to produce 8-fluoro-2-{4-[(methylamino)methyl]phenyl}-1,3,4,5-tetrahydro-6H-azepino[5,4,3-cd]indol-6-one.

7. The method of claim 6, wherein the step b) comprises a CuI-promoted indole formation.

8. The method of claim 6, wherein the step e) comprises hydrogenation.

* * * * *